United States Patent [19]

Revici

[11] Patent Number: 4,649,152

[45] Date of Patent: Mar. 10, 1987

[54] COMPOSITION AND METHOD FOR TREATMENT OF POTASSIUM DEFICIENCY

[75] Inventor: Emanuel Revici, New York, N.Y.

[73] Assignee: Elena Avram, New York, N.Y.

[21] Appl. No.: 782,662

[22] Filed: Oct. 1, 1985

[51] Int. Cl.⁴ .............................................. A61K 31/40
[52] U.S. Cl. .................................................... 514/425
[58] Field of Search ......................................... 514/425

*Primary Examiner*—Stanley J. Friedman

*Attorney, Agent, or Firm*—Pennie & Edmonds

[57] ABSTRACT

A method for making a composition containing a fatty acid or fatty ester compound and potassium. The compositions produced by the method. Administration of these compositions to a patient to increase the potassium content of cells or tissue having a potassium deficiency or to treat at least some of the symptoms of diseases or adverse effects caused by this potassium deficiency.

20 Claims, No Drawings

COMPOSITION AND METHOD FOR TREATMENT OF POTASSIUM DEFICIENCY

TECHNICAL FIELD

The present disclosure concerns a method to treat various conditions resulting from potassium deficiency and preparations for same.

BACKGROUND

It is known that the abnormal cells in general and the neoplastic cells in particular are poor in potassium, a fact which is considered as including and enhancing their abnormal character. It is also known that the blood plasma of subjects with such abnormal conditions is especially rich in potassium, apparently due to the body's attempt to correct the cellular potassium deficiency. The form under which the potassium is circulating in the blood, that is, mainly as ceruloplasmin, however, is not the proper form from which the potassium can be taken by the abnormal cells.

SUMMARY OF THE INVENTION

The invention comprises novel compositions of fatty acids, ester, or oils which include potassium incorporated therein. These composition are made by heating the oil component to a temperature of at least above 230° C. for a sufficient time to incorporate a predetermined amount of potassium into the oil. At least about 0.1% can be used, although between 1 and 10% is preferred.

These compositions of the invention may be administered to a patient who has cells or tissue which are deficient in potassium to increase the potassium content as well as to treat the symptoms of diseases or adverse effects caused by the potassium deficient cells or tissue.

DETAILED DESCRIPTION OF THE INVENTION

I have found that in general, the abnormal cells and tissues in the body have free lipids. Thus, a lipid or compound having a lipidic character introduced into the body can be selectively taken by the abnormal cells. Accordingly, it is believed that a potassium compound having lipidic properties is useful as a therapeutic agent for patients who have such abnormal cells.

I have found that potassium can be incorporated in the molecule of a fatty acid by heating together an organic or inorganic salt of potassium with a fatty acid or its oil. Preferably, the fatty acid or oil is previously oxidized by being heated and mixed with air or oxygen. The mixtures of potassium and fatty acids or oil are heated at a temperature above about 230° C. for a time until an exothermic reaction is observed, which reaction indicates that the incorporation is taking place.

Examples of the potassium/fatty acid or oil compositions that can be used according to the invention include the reaction products of allylic unsaturated fatty acids or esters and a potassium salt. These reaction products are produced by heating a liquid composition containing a fatty acid or fatty ester, structurally characterized by allylic unsaturation with a potassium salt. Applicant believes that any potassium salt may be used in this invention. Preferably, the potassium salt is an organic potassium salt such as potassium acetate or potassium carbonate, and the liquid is preferably oxidized for example, by bubbling air or oxygen through the reaction mixture.

The allylically unsaturated compound is preferably a naturally occurring oil containing polyunsaturated fatty esters, such as an animal, vegetable, or fish oil, and, particularly, polyunsaturated vegetable oils. Sesame oil, a vegetable oil consisting largely of triglycerides, is the most advantageous composition found to date in the practice of this invention.

The composition utilized should contain a significant percentage of molecular species having allylic moieties to render the compositions useful according to the invention. Such moieties are indicated by the following partial structures —CH=CH—CH$_2$—CH=CH— and/or —CH=CH—CH=CH—CH$_2$—. As indicated, the unsaturation can be conjugated or nonconjugated, but the composition must contain allylic methylene hydrogen.

Such compositions may initially be oxidized or heated in the presence of air or oxygen at the temperature range between about 100° C. and about 150° C. The oxygen can be obtained by merely heating the composition in a vessel which is open to the atmosphere, but preferably and advantageously, the source of oxygen is a gas such as air which is injected into the heated oil. Introduction of air also provides a source of agitation.

The heating step is conducted for a period of from about 15 minutes to about two hours. The temperature should be maintained at an upper limit within the range of about 230° C. to 250° C., and preferably about 235° C. to 240° C. These temperature limitations are based on a heating time of about one-half hour. The temperatures can be altered within limits depending on the time of heating. For example, when the temperature is about 235° C., the time is about one-half hour, while temperatures as high as 250° C. require a shorter period of time for heating. Higher temperatures for a prolonged period of time tend to degrade the composition and should thus be avoided.

Agitation, by stirring for example, aids in the reaction, and experiments to date indicate that a fairly violent stirring is advantageous. The introduction of air into the mixture during the heating is also very advantageous, particularly when the mixture is not subjected to prolonged heating and thus, is the preferred method. The mixing or stirring can be accomplished with the introduction of the air.

After the reaction has taken place, the mixture is cooled. The remaining fluid is ready for use after appropriate sterilization for injection or incorporated into capsules, such as gelatin, for oral administration.

The precise nature of the compositions which result from the above-described treatment or the identity of the effective component or components is not presently known. It is known, however, that these compositions do include potassium and that a proportion of potassium in the range of about 1 to 10 weight percent has been found to be effective.

As mentioned above, although any potassium salt may be used, an organic salt of potassium, such as potassium carbonate or potassium acetate, is preferred, with the potassium bonding the eleostearic acid present in this oil. Although any amount above 0.1% of potassium incorporated into the composition is useful, the preferred amount ranges between about 1 to 10 weight percent.

The products obtained have the potassium incorporated in general at the level of the double bonds of the different unsaturated fatty acids, this causes their toxicity to be exceptionally low. The injection of 1 ml of a product having 5% potassium to a mouse does not kill it.

The incorporated potassium composition may be administered orally, by injections, sublingually or rectally in the appropriate formulation.

The incorporated potassium is believed to be absorbed by the abnormal cells, thus compensating for their low potassium content. This treatment produces objective and subjective improvement in the conditions, of patients having a variety of diseases based upon such abnormal cells. The neoplastic diseases are examples of diseased in which low cellular potassium abnormal cells are found.

Such low cellular potassium abnormal cells are believed to cause an catabolic imbalance in the body. This catabolic imbalance can be analyzed and diagnosed by blood and urine analyses. A low eosinophilia (below 100/cmm), a high red cell sedimentation rate (above 15 ml/1 hour), a high serum potassium (above 4.5 mEq), a urinary acid pH (below 7), high specific gravity (above 1.016), low surface tension (below 89 dynes/cm), and low calcium or chloride excretion are indications of an catabolic imbalance. (The opposite analyses would indicate a anabolic imbalance.)

These analyses and clinical manifestations have to be changed by the administration of the incorporated potassium compound. In a 5% potassium incorporated preparation, amounts from about 1/10 to 2 ml daily are predilectly used for the treatment of this catabolic imbalance. For other conditions with anabolic imbalances, doses from about 2 to 10 ml daily are predilectly used. In general the higher the dose used, the better are the clinical results.

Interesting results are those concerning pain, the changes induced in the lesions manifesting first an action upon pain. Manifest changes in the tumors and in the subjective manifestations of the neoplastic diseases are obtained even in a very short time. Thus, the incorporated potassium appears as a predilect treatment of the symptoms of neoplastic conditions, and possibly to the treatment of such condition themselves.

Good results were also obtained in the use of the incorporated potassium compounds for the different manifestations of AIDS (acquired immune deficiency syndrome) as well as for the ARC (AIDS related complex).

Interesting also are the results in almost all the different conditions, such as neurological conditions, epilepsy and others, the problem of cellular potassium deficiency being a general pathological occurrence. Interesting is the action of the lipidic potassium products on the viral infections.

The incorporated potassium composition may be administered together with different other agents.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A method for making a composition which comprises:

selecting at least one fatty acid or fatty ester compound having an allylic unsaturation of the type —CH=CH—CH$_2$—CH=CH— or —CH=CH—CH=CH—CH$_2$—;

adding to said compound a potassium salt to form a mixture;

heating said mixture above about 230° C. for a sufficient period of time to incorporate at least about 0.1% by weight potassium into the compound;

cooling the mixture; and recovering the potassium-incorporated compound as the remaining fluid of the mixture.

2. The method of claim 1 wherein the fatty acid or fatty ester compound is oxidized by mixing the compound with air and heating the mixture.

3. The method of claim 1 wherein the fatty acid or fatty ester compound is heated at a temperature range of about 230° to 250° C. for a time of about one-half hour so as to incorporate at least 1% by weight potassium into the composition.

4. A method for making a composition which comprises:

selecting a vegetable oil;

adding to said oil an organic potassium salt to form a mixture.

heating said mixture at a temperature of above about 230° C. for a sufficient period of time to incorporate about 1% by weight potassium into the oil;

cooling the mixture; and recovering the potassium-incorporated oil as the remaining fluid of the mixture.

5. A method for making a composition which comprises:

mixing sesame seed oil, air, and potassium carbonate or potassium acetate to form a mixture;

heating said mixture at a temperature from about 230° to 250° C. for about one-half hour to incorporate at least about 1% by weight potassium into the oil;

agitating the mixture during the heating step;

cooling the mixture; and recovering the potassium-incorporated oil as the remaining fluid of the mixture.

6. The composition produced by the method of claim 1.

7. The composition produced by the method of claim 4.

8. The composition produced by the method of claim 5.

9. A method for increasing the potassium content of cells or tissue having a potassium deficiency which comprises administering to a patient having said potassium deficient cells or tissue a sufficient amount of the composition of claim 6.

10. A method for increasing the potassium content of cells or tissue having a potassium deficiency which comprises administering to a patient having said potassium deficient cells or tissue a sufficient amount of the composition of claim 7.

11. A method for increasing the potassium content of cells or tissue having a potassium deficiency which comprises administering to a patient having said potassium deficient cells or tissue a sufficient amount of the composition of claim 8.

12. A method for treating at least one of the symptom of diseases or adverse effects in a patient caused by cells having a potassium deficiency which comprises administering to said patient a sufficient amount of the composition of claim 6.

13. A method for treating at least one of the symptoms of diseases or adverse effects in a patient caused by cells having a potassium deficiency which comprises administering to said patient a sufficient amount of the composition of claim 7.

14. A method for treating at least one of the symptoms of diseases or adverse effects in a patient caused by cells having a potassium deficiency which comprises administering to said patient a sufficient amount of the composition of claim 8.

15. The method of claim 9 wherein about 1/10 to 10 ml of the composition is daily administered to the patient.

16. The method of claim 10 wherein about 1/10 to 10 ml of the composition is daily administered to the patient.

17. The method of claim 11 wherein about 1/10 to 10 ml of the composition is daily administered to the patient.

18. The method of claim 12 wherein about 1/10 to 10 ml of the composition is daily administered to the patient.

19. The method of claim 13 wherein about 1/10 to 10 ml of the composition is daily administered to the patient.

20. The method of claim 14 wherein about 1/10 to 10 ml of the composition is daily administered to the patient.

* * * * *